(12) United States Patent
Qi et al.

(10) Patent No.: US 12,281,337 B2
(45) Date of Patent: Apr. 22, 2025

(54) GDSL LIPASE, GENETICALLY-ENGINEERED BACTERIA AND APPLICATION THEREOF

(71) Applicants: Suzhou Kemanduo Biotechnology Co., Ltd., Suzhou (CN); Changshu Institute of Technology, Suzhou (CN)

(72) Inventors: Bin Qi, Suzhou (CN); Manting Qi, Suzhou (CN); Limei Wang, Suzhou (CN); Yuhua Wang, Suzhou (CN)

(73) Assignees: Suzhou Kemanduo Biotechnology Co., Ltd., Suzhou (CN); Changshu Institute of Technology, Suzhou (CN)

( * ) Notice: Subject to any disclaimer, the term of this patent is extended or adjusted under 35 U.S.C. 154(b) by 0 days.

(21) Appl. No.: 18/341,792

(22) Filed: Jun. 27, 2023

(65) Prior Publication Data

US 2024/0011001 A1    Jan. 11, 2024

Related U.S. Application Data

(63) Continuation of application No. 17/279,733, filed as application No. PCT/CN2019/114789 on Oct. 31, 2019, now abandoned.

(30) Foreign Application Priority Data

Mar. 15, 2019   (CN) .................. 201910199413.X

(51) Int. Cl.
| | | |
|---|---|---|
| *C12N 9/20* | (2006.01) | |
| *C12P 7/64* | (2022.01) | |
| *C12P 7/6436* | (2022.01) | |

(52) U.S. Cl.
CPC .............. *C12N 9/20* (2013.01); *C12P 7/6436* (2013.01)

(58) Field of Classification Search
CPC ................................. C12N 9/20; C12P 7/6436
See application file for complete search history.

(56) References Cited

PUBLICATIONS

Li. CP031742.1. GenBank Database. Aug. 27, 2018.*
Ichikawa. GFH64141. GenBank Database. Aug. 25, 2023.*

* cited by examiner

*Primary Examiner* — Yong D Pak
(74) *Attorney, Agent, or Firm* — Proi Intellectual Property US

(57) ABSTRACT

The invention relates to a GDSL lipase, genetically-engineered bacteria and an application thereof. The GDSL lipase is derived from *Streptomyces diastaticus* CS1801 and its amino acid sequence is as shown in SEQ ID NO.2. After construction of a genetically-engineered bacterium strain, a GDSL lipase is generated through fermentation. Through this enzyme, vitamin A and palmitic acid are converted to produce vitamin A palmitate. The content of the vitamin A palmitate obtained from the conversion is 16.35 mg/L at most. The conversion efficiency is 81.75% at most. This lipase provides a new path to synthesize vitamin A palmitate by the enzymatic method and has an important application prospect.

9 Claims, 2 Drawing Sheets
Specification includes a Sequence Listing.

GDSL LIPASE, GENETICALLY-ENGINEERED BACTERIA AND APPLICATION THEREOF

This application is a Continuation of U.S. patent application Ser. No. 17/279,733, filed Mar. 25, 2021, which is the US national phase of International application PCT/CN2019/114789 filed on Oct. 31, 2019 which claims priority of Chinese patent application CN 201910199413.X filed on Mar. 15, 2019, herein incorporated by reference in their entirety.

TECHNICAL FIELD

The present invention relates to the fields of genetic engineering and protein engineering and to a method for gene cloning and expression of a new type of GDSL lipase and an application in the production of vitamin A palmitate by the enzymatic method and pertains to a technology in the industrial microorganism field.

BACKGROUND ART

Lipase, also known as triacylglycerol lipase, is a type of enzymes that can degrade natural oils into glycerol and free fatty acids. It is widely found in animals, plants and microorganisms. Microorganisms are an important source of lipase, mainly including *Rhizopus, Aspergillus* and *Candida*. According to the analysis of the amino acid sequences of different lipases and their basic biological properties, lipases can be divided into eight families, of which the second family is also known as a GDSL family. GDSL lipase (lipase, EC 3.1.1.3) is a type of hydrolase that can hydrolyze various substrates such as thioesters, aryl esters, phospholipids and amino acids. As GDSL lipase is a new type of lipase, little research has been done on its expression and function. Because GDSL lipase has ester hydrolysis activity, people are deepening the research on it.

Vitamin A palmitate can help maintain normal visual function and participate in various metabolic activities to maintain the health of the organisms. It is currently the most commonly used vitamin A derivative and is widely used in various industries such as food, cosmetics and medicine. At present, vitamin A palmitate is synthesized mainly by the chemical method and the enzymatic method. The chemical method for the synthesis of vitamin A palmitate has problems such as environmental pollution and cost, while the enzymatic method features less pollution, high space-time yield and low cost. The enzyme that is used to produce vitamin A palmitate is a lipase with ester hydrolysis activity.

SUMMARY OF THE INVENTION

The object of the present invention is to provide a GDSL lipase, genetically-engineered bacteria and an application thereof. The lipase has high activity and can be used in the production of vitamin A palmitate.

In order to achieve the above object, the present invention adopts the following technical solution:

A GDSL lipase, wherein its amino acid sequence is as shown in SEQ ID NO.2.

The present invention further provides a gene encoding the foregoing GDSL lipase.

Specifically, the nucleotide sequence of the gene encoding the GDSL lipase is as shown in SEQ ID NO.1.

The foregoing GDSL lipase is derived from *Streptomyces diastaticus* CS1801, which has been disclosed in the applicant's prior application CN109337843A.

The present invention further provides a recombinant vector, comprising the gene encoding the GDSL lipase and an expression vector, and the nucleotide sequence of the gene is as shown in SEQ ID NO.1. The expression vector is pET-32a (+). The foregoing gene is inserted between multiple cloning sites of the expression vector pET-32a (+).

The present invention further provides a genetically-engineered bacterium containing the foregoing recombinant vector.

Further, the host cell of the engineered bacterium is *E. coli* BL21(DE3).

The present invention further provides an application of the foregoing engineered bacterium in the production of vitamin A palmitate by the enzymatic method, including:

(1) inoculating the engineered bacterium to an LB medium for seed culture;
(2) transferring the seed solution to a fermentation medium for fermentation culture, and then adding an inducer to induce expression of enzymes;
(3) centrifuging the fermentation broth to obtain a supernate, and obtaining enzyme powder through precipitation by ammonium sulfate and lyophilization; and
(4) adding the enzyme powder to an organic phase system containing vitamin A and palmitic acid to produce vitamin A palmitate.

Specifically, the method includes: inoculating the engineered bacteria cultured in an LB medium at 37° C., 200 r for 8~12 h to a fermentation medium in an inoculum size of 5%; fermenting them for 8~12 h, then adding IPTG till a final concentration of 0.4~1 mmol/L and fermenting and culturing at 37° C., 200 r for 18~24 h; centrifuging at 4000 r for 10 min to obtain a supernate of the fermentation broth; precipitating zymoprotein by 50% ammonium sulfate and lyophilizing the precipitate for 48 h to obtain enzyme powder; and adding the enzyme powder to an organic phase system (vitamin A:palmitic acid=10 g: 10 g, dissolved in 1 L of normal hexane) at a ratio of 5%, and determining the content of vitamin A palmitate and calculating the conversion rate after a specific time of conversion.

Further, the fermentation medium comprises:
tryptone 10 g/L, yeast powder 5 g/L, NaCl 10 g/L, $MgSO_4 \cdot 7H_2O$ 1 g/L, $KH_2PO_4$ 0.5 g/L, $K_2HPO_4$ 0.5 g/L, and olive oil emulsion 12 mL/L.

Further, an olive oil emulsifier is prepared by the following method: mixing olive oil emulsifier PVA with olive oil at a volume ratio of 3:1 and emulsifying the mixture by ultrasound.

The genetically-engineered bacterium constructed by the enzyme in the present invention is used to produce vitamin A palmitate by the enzymatic method. The content of the vitamin A palmitate obtained from conversion is 16.35 mg/L at most. The maximum conversion rate is 81.75%. This lipase provides a new path to synthesize vitamin A palmitate by the enzymatic method and has an important application prospect.

DETAILED DESCRIPTION OF PREFERRED EMBODIMENTS

Embodiment 1

This embodiment describes a method for PCR amplification of GDSL lipase derived from *Streptomyces diastaticus*.

*Streptomyces diastaticus* CS1801 stored on a test tube slant is used for plate activation, and a single colony is inoculated to an LB liquid medium and cultured at 30° C. for 2~3 days. The culture solution is centrifuged at 8000 r for 2 min, thalli are collected and a bacterial genome extraction kit is used for total genome extraction. The extraction steps are described in the bacterial genome extraction kit manual of Sangon Biotech (Shanghai) Co., Ltd.

The primers for GDSL lipase gene amplification are designed as follows:

```
GDSL2-up:
                                      (SEQ ID NO: 3)
5,-GTGGCCGGGCTCACGTCCTC-3,

GDSL2-down:
                                      (SEQ ID NO: 4)
5,-TCATTCCGGCAGGCTCCG-3,
```

The extracted *Streptomyces diastaticus* genome is used as a template, and the above primers and a PCR amplification kit with high GC content from Sangon Biotech (Shanghai) Co., Ltd. are used for amplification, but no Taq enzyme is added.

The specific amplification procedure is as follows: pre-denature at 95° C. for 10 min and add Taq enzyme; denature at 95° C. for 1 min, anneal at 55° C. for 30 s, extend at 72° C. for 1 min, repeat this process for 29 cycles and lastly extend at 72° C. for 30 min; and take the product to perform agarose gel electrophoresis (AGE), cut gel and extract and store target strips. The gel extraction kit is purchased from Sangon Biotech (Shanghai) Co., Ltd.

Embodiment 2

This embodiment describes the PCR amplification method of GDSL lipase gene with restriction enzyme cutting sites.

The primers for amplification of GDSL lipase gene with restriction enzyme cutting sites are designed as follows:

```
GDSL2-up:
                                      (SEQ ID NO: 5)
5,-CCGGAATTCGTGGCCGGGCTCACGTCCTC-3,

GDSL2-down:
                                      (SEQ ID NO: 6)
5, -CCGCTCGAGTCATTCCGGCAGGCTCCG-3,
```

The gel extraction product in Embodiment 1 is used as a template, and the above primers and a PCR amplification kit with high GC content from Sangon Biotech (Shanghai) Co., Ltd. are used for amplification.

Figure 1:
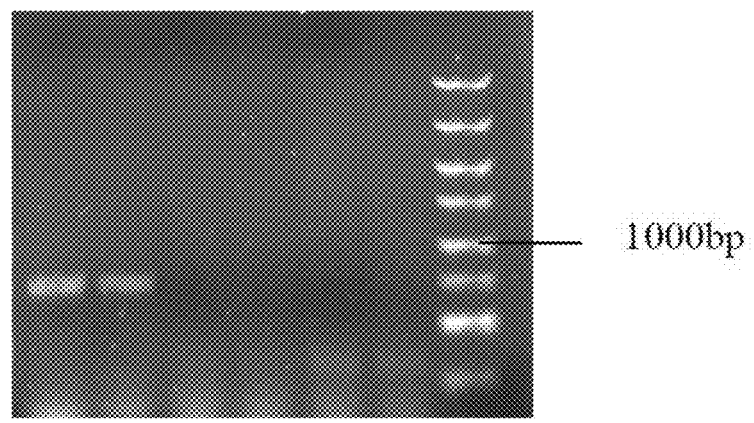
FIG. 1 shows target strips of PCR amplification of GDSL lipase.

The specific amplification procedure is as follows: pre-denature at 95° C. for 2 min; denature at 95° C. for 1 min, anneal at 55° C. for 30 s, extend at 72° C. for 1 min, repeat this process for 29 cycles and lastly extend at 72° C. for 30 min; and take the product to perform agarose gel electrophoresis (AGE), and cut gel, extract the target strips as shown in FIG. 1 and send them to Sangon Biotech (Shanghai) Co., Ltd. for sequence measurement to obtain sequence SEQ ID NO.1.

Embodiment 3

This embodiment describes a method for constructing a recombinant cloning vector of GDSL lipase.

The gel extraction product in Embodiment 2 is linked to a T vector. After conversion to DH-5α, positive clones are picked for verification. After extraction of plasmid, the sequence is measured for verification.

Embodiment 4

This embodiment describes a method for constructing a recombinant expression vector of GDSL lipase.

XhoI and EcoRI are used to perform double digestion of the plasmid in Embodiment 3 and extract target strips, meanwhile XhoI and EcoRI are used to perform double digestion of pET32a(+) vector and extract large fragments in the vector, the extracted target gene fragments are linked to vector fragments and they are imported to host cell *E. coli* DH5α. After resistance screening, positive clones are picked to measure the sequence for verification.

Embodiment 5

This embodiment describes a method for constructing genetically-engineered bacteria of GDSL lipase.

Figure 2:
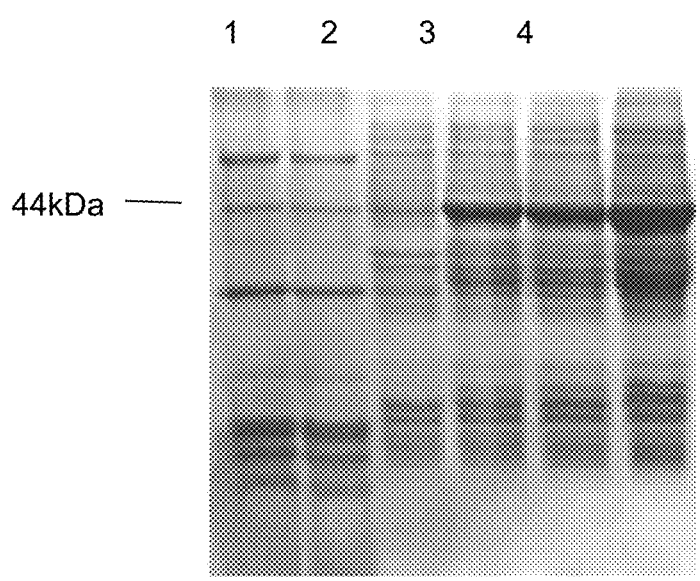
FIG. 2 is an SDS-PAGE electrophoretogram of *E. coli*.

The plasmid of the positive clones with a correct sequence in Embodiment 4 is extracted and directly converted and imported to host cell *E. coli* BL21 (DE3). Genetically-engineered bacteria of GDSL lipase are successfully constructed. In the fermentation process, an inducer like IPTG needs to be added to efficiently express GDSL lipase protein. Through SDS-PAGE, it is verified that the fusion protein is successfully expressed. SDS-PAGE electrophoretogram is as shown in FIG. 2, lane 1 is *E. coli* pET32a-GDSL not induced, and lanes 2, 3 and 4 are recombinant *E. coli* pET32a-GDSL that has been induced by IPTG for 4, 8 and 16 h, respectively. Compared with other lanes, obvious strips are found at molecular weight 44k Da. After removal of the fusion expression protein on the plasmid, it is consistent with the predicted target protein in size, suggesting that GDSL lipase is successfully expressed in recombinant bacteria.

Embodiment 6

This embodiment describes an application of genetically-engineered bacteria of GDSL lipase in vitamin A palmitate.

(1) Inoculate the genetically-engineered bacteria cultured in an LB medium at 37° C., 200 r for 8~12 h to a fermentation medium in an inoculum size of 5%.

(2) Ferment them for 8~12 h, add IPTG till a final concentration of 0.4~1 mmol/L, and ferment and culture at 37° C., 200 r for 18~24 h.

(3) Centrifuge at 4000 r for 10 min to get a supernate of the fermentation broth; use a 50% ammonium sulfate solution to precipitate zymoprotein, lyophilize it for 48 h to obtain enzyme powder, and determine the enzyme activity of GDSL lipase according to the national standard GBT23535-2009, which is 1.53 U/mg.

Figure 3:
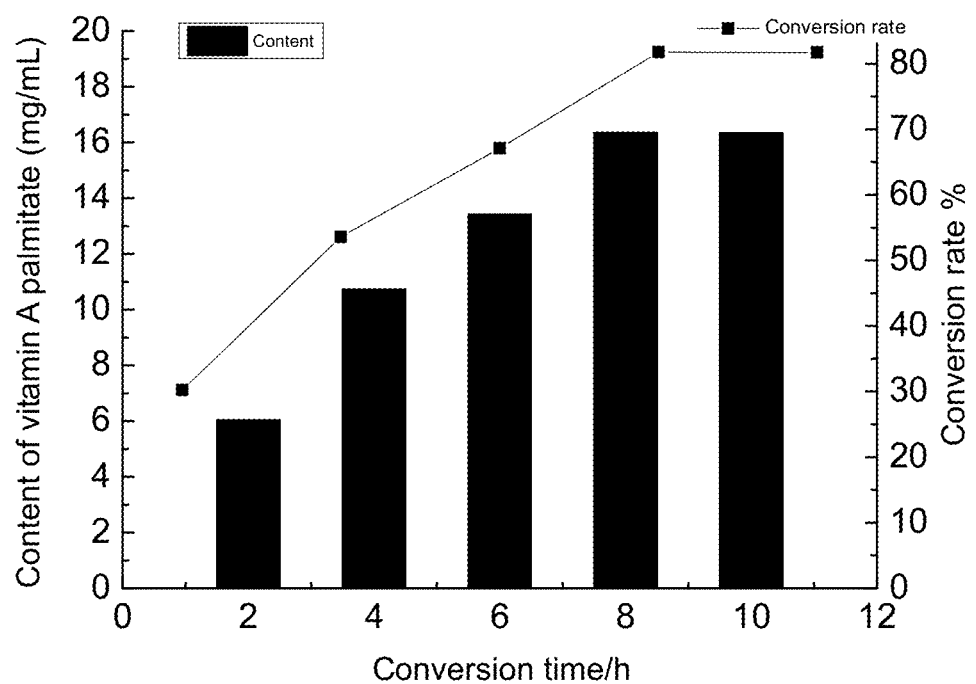
FIG. 3 shows the conversion time of GDSL lipase in the production of vitamin A palmitate.

(4) Add 5% (w/v) enzyme powder to an organic phase system (vitamin A:palmitic acid=10 g: 10 g, dissolved in 1 L of normal hexane), determine the content of vitamin A palmitate after 2, 4, 6, 8 and 10 h of conversion and calculate the conversion rates. As shown in FIG. 3, after 8 h of conversion, the content of vitamin A palmitate is 16.35 mg/L at most and the conversion rate is 81.75%.

The fermentation medium comprises:

tryptone 10 g/L, yeast powder 5 g/L, NaCl 10 g/L, $MgSO_4 \cdot 7H_2O$ 1 g/L, $KH_2PO_4$ 0.5 g/L, $K_2HPO_4$ 0.5 g/L, olive oil emulsion 12 mL/L, and distilled water added till volume 1 L.

The olive oil emulsion is prepared by the following method: mixing olive oil emulsifier PVA with olive oil at a volume ratio of 3:1 and emulsifying the mixture by ultrasound.

The vitamin A palmitate is determined by HPLC and quantitatively determined by the external standard method. Chromatographic conditions: chromatographic column: Alltech C18 (250×4.6 mm, 4.5 μm); mobile phase: 100% methanol; detector: Shimadzu 10 A ultraviolet detector; detection wavelength: 327 nm; flow rate: 1 mL/min.

Calculation formula of conversion rate:

$$\text{Conversion rate} = \frac{\text{Vitamin A palmitate (g/L)}}{(\text{Vitamin A (g)} + \text{palmitic acid (g)})/n\text{-hexane (L)}} \times 100\%$$

SEQUENCE LISTING

```
Sequence total quantity: 2
SEQ ID NO: 1            moltype = DNA  length = 741
FEATURE                 Location/Qualifiers
source                  1..741
                        mol_type = other DNA
                        organism = synthetic construct
CDS                     1..741
                        note = The sequence is synthesized
SEQUENCE: 1
gtggccgggc tcacgtcctc ggtgccgcgc cgctgggaga tgatgctgcc catgcgcttc    60
ctcttcgtcg gcgactccat gacggtcggc cgggccgggg acttcacctg gcgccaccgc   120
atgtggcagc acctggagac gacccctcgg ccccggcgcgt acaccatcac cggccccgc   180
accggcctgt acgcgggcga cggcgccgac gcctccgagg cgtacgcgga ccccgccttc   240
ccgcccgccg cgcgccgcca cctcgcgggc tggggcgagg ggtggcggca catggccccg   300
ctgatccagc cggtcgtcgc caccacccgc gccgacgtgc tgctggtcgc cctcggcctg   360
atcgacctcg gcttctacgc ccacgccgag gagaccgccg agcacgcccg gaccttcctg   420
tcccgggccc gcgccgccaa gccggacgta cgcgccgtca tcctcccggt cgtccccaac   480
gtccgcgccc gcaccgaccc cttcttcgcc gacgactgcg cccgcttcaa cacgctcctc   540
gccaagaccg tcgccgagct ggaccgcccc ggctccccgc tcctgctcgc ctcccacccg   600
cccggctaca ccctggacgc cgacacctac gacggcaccc atcccggtcc ctccggcgaa   660
caccgcatcg ccgccgcctt cgccgacgcg ctgcaccagg gctggggcgt cggcgggccg   720
taccggagcc tgccggaatg a                                              741

SEQ ID NO: 2            moltype = AA   length = 246
FEATURE                 Location/Qualifiers
REGION                  1..246
                        note = The sequence is synthesized
source                  1..246
                        mol_type = protein
                        organism = synthetic construct
SEQUENCE: 2
VAGLTSSVPR RWEMMLPMRF LFVGDSMTVG RAGDFTWRHR MWQHLETTLG PGAYTITGPR     60
TGLYAGDGAD ASEAYADPAF PPAARRHLAG WGEGWRHMAP LIQPVVATTR ADVLLVALGL   120
IDLGFYAHAE ETAEHARTFL SRARAAKPDV RAVILPVVPN VRARTDPFFA DDCARFNTLL   180
AKTVAELDRP GSPLLLASHP PGYTLDADTY DGTHPGPSGE HRIAAAFADA LHQGWGVGGP   240
YRSLPE                                                                246
```

What is claimed is:

1. A method for production of vitamin A palmitate, comprising:
   (1) inoculating an engineered bacterium containing a recombinant vector comprising the GDSL lipase nucleotide sequence of SEQ ID NO:1 into an LB medium for seed culture;
   (2) transferring the seed solution to a fermentation medium for fermentation culture, and then adding an inducer to induce expression of the GDSL lipase nucleotide sequence of SEQ ID NO:1;
   (3) centrifuging the fermentation broth to obtain a supernate, and obtaining GDSL lipase powder through precipitation by ammonium sulfate and lyophilization; and
   (4) adding the GDSL lipase powder to an organic phase system containing vitamin A and palmitic acid to produce vitamin A palmitate.

2. The method according to claim 1, wherein the fermentation medium comprises:
   tryptone 10 g/L, yeast powder 5 g/L, NaCl 10 g/L, $MgSO_4 \cdot 7H_2O$ 1 g/L, $KH_2PO_4$ 0.5 g/L, $K_2HPO_4$ 0.5 g/L, olive oil emulsion 12 mL/L, and distilled water added till volume 1 L.

3. The method according to claim 2, wherein the olive oil emulsion is prepared by the following method: mixing olive oil emulsifier PVA with olive oil at a volume ratio of 3:1 and emulsifying the mixture by ultrasound.

4. The method of claim 1, wherein the recombinant vector is the expression vector pET 32a(+).

5. The method of claim 1, wherein the bacterium is *E. coli* BL21 (DE3).

6. The method of claim 1, wherein the step of inoculating further comprises inoculating the engineered bacteria at 37° C., 200 r for 8~12 hours.

7. The method of claim 1, wherein the step of transferring further comprises fermenting the seed solution for 8~12 hours.

8. The method of claim 7, further comprising adding IPTG into the fermented seed solution till a final concentration of 0.4~1 mmol/L.

9. The method of claim 8, further comprising fermenting and culturing the fermented seed solution at 37° C., 200 r for 18~24 hours.

* * * * *